United States Patent
Mech

(10) Patent No.: US 9,144,592 B2
(45) Date of Patent: Sep. 29, 2015

(54) DIETARY SUPPLEMENT WITH PROTEIN ACTIVATOR

(71) Applicant: Gianluca Mech, Meledo di Sarego (IT)

(72) Inventor: Gianluca Mech, Meledo di Sarego (IT)

( * ) Notice: Subject to any disclaimer, the term of this patent is extended or adjusted under 35 U.S.C. 154(b) by 10 days.

(21) Appl. No.: 14/022,700

(22) Filed: Sep. 10, 2013

(65) Prior Publication Data

US 2014/0010921 A1 Jan. 9, 2014

Related U.S. Application Data

(62) Division of application No. 12/444,225, filed as application No. PCT/IB2007/052355 on Jun. 19, 2007, now Pat. No. 8,557,303.

(30) Foreign Application Priority Data

Oct. 6, 2006 (IT) .............................. SM2006A0031

(51) Int. Cl.

| | | |
|---|---|---|
| A61K 36/00 | (2006.01) | |
| A61K 36/708 | (2006.01) | |
| A61K 36/886 | (2006.01) | |
| A61K 36/235 | (2006.01) | |
| A61K 36/268 | (2006.01) | |
| A61K 36/53 | (2006.01) | |
| A61K 36/9066 | (2006.01) | |
| A61K 36/48 | (2006.01) | |
| A61K 36/72 | (2006.01) | |
| A61K 36/70 | (2006.01) | |
| A61K 36/906 | (2006.01) | |
| A61K 36/23 | (2006.01) | |
| A61K 36/28 | (2006.01) | |
| A61K 36/31 | (2006.01) | |
| A23L 1/29 | (2006.01) | |
| A23L 1/30 | (2006.01) | |
| A23L 1/305 | (2006.01) | |

(52) U.S. Cl.
CPC ................. *A61K 36/48* (2013.01); *A23L 1/293* (2013.01); *A23L 1/3002* (2013.01); *A23L 1/305* (2013.01); *A23L 1/3055* (2013.01); *A23L 1/3056* (2013.01); *A61K 36/23* (2013.01); *A61K 36/28* (2013.01); *A61K 36/31* (2013.01); *A61K 36/53* (2013.01); *A61K 36/70* (2013.01); *A61K 36/72* (2013.01); *A61K 36/906* (2013.01); *A23V 2002/00* (2013.01)

(58) Field of Classification Search
None
See application file for complete search history.

(56) References Cited

U.S. PATENT DOCUMENTS

| 5,569,458 A | 10/1996 | Greenberg |
|---|---|---|
| 5,902,617 A | 5/1999 | Pabst |
| 2004/0253295 A1 | 12/2004 | Martin et al. |

FOREIGN PATENT DOCUMENTS

| EP | 1604677 A1 | 12/2005 |
|---|---|---|
| GB | 2120522 A | 12/1983 |
| WO | 01/74169 A1 | 10/2001 |
| WO | 03/037320 A1 | 5/2003 |
| WO | 2004/014153 A1 | 2/2004 |
| WO | 2008/011700 A1 | 1/2008 |

*Primary Examiner* — Qiuwen Mi
(74) *Attorney, Agent, or Firm* — Tutunjian & Bitetto, P.C.

(57) ABSTRACT

A dietary supplement includes a base mixture of ingredients with at least one plant or animal protein and a plant-based protein activator. The plant-based protein activator includes a first group of plant extracts having a proteolytic activity and possibly a second group of plant extracts with an emollient and peristaltic activity, a third group of plant extracts with a carminative activity and a fourth group of plant extracts with a depurative and liver and kidney protective activity.

19 Claims, No Drawings

DIETARY SUPPLEMENT WITH PROTEIN ACTIVATOR

CROSS-REFERENCE TO RELATED APPLICATIONS

This is a division of application Ser. No. 12/444,225 filed Dec. 28, 2009 which is the U.S. National Stage application of PCT/IB2007/052355 filed on Jun. 19, 2007, the disclosure of which is incorporated herein by reference.

FIELD OF THE INVENTION

The present invention finds application in the field of dietary supplements and particularly relates to a dietary supplement with a plant-based protein activator.

BACKGROUND OF THE INVENTION

It is known that many weight loss diet plans are based on reduced caloric intake, as obtained by a more or less balanced reduction of the amount of ingested food. This method may lead to a general deficiency of proteins, glucides, vitamins and mineral salts, with detrimental effects on the organism and with the risk that, once the diet ends, the lost weight will be easily regained, also due to psychosomatic factors.

Furthermore, for a low calorie diet to be balanced especially when adopted under medical control, it has to be followed very slow, with the diet cycle becoming unacceptably long for many subjects.

Another drawback of this kind of diet is that when a human body is subjected to a low caloric intake, it reacts by decreasing fat consumption and slowing down the basal metabolism which represents about 70% of the total consumption in mammals and human beings, thereby causing a reduction of the lean body mass and the muscle tone, as well as tiredness and over-fatigue sensations.

Furthermore, once the diet cycle has ended, recovery of the lean body mass requires accumulation of larger amounts of fat mass, which induces the so-called "yo-yo effect". After an off period, the cycle is thus repeated with the same effects, and this leads to progressive damaging of the muscle mass and health of the subject.

Meal replacements, such as the typical nutritionally balanced bars have been introduced to simplify and improve low calorie diets. Consumption of these meals can correspond to a classical balanced reduction of caloric intake or a "normal calorie" diet, and has the advantage of being practical and ensuring correct dosing, while avoiding the need of weighing food. This "normal calorie" balanced diet is an optimal solution to maintain one's own ideal weight and health but not to lose weight in a controlled and healthy manner.

For effective and healthy weight loss, the caloric intake has to be reduced in response to each individual's needs, while following a varied and balanced diet, and preserving the lean body mass and the vital parts of the body. This goal may be achieved by creating some food deficiency, which has to be sharply targeted and not generalized, without suppressing proteins, vitamins, mineral salts, that are indispensable for normal operation of vital organs, for support to the musculature and for body tone. Particularly, the fats and sugars will have to be reduced, but not suppressed.

Therefore, an ideal weight loss diet shall provide a reduced caloric intake while ensuring that the body receives proper amounts of proteins, mineral salts, fats and sugars. No natural food has been known heretofore that combines all the above features while allowing weight loss.

Protein supplements have been known and widely used for many years, especially by sportsmen and body-builders.

These supplements, which typically contain essentially large amounts of proteins to increase the muscle mass and creatine provide more energy during sports performances, as well as antioxidants, vitamins and other microadditives. These protein supplements are perfectly functional to enhance the athletes' performances but not to lose weight. Furthermore, these supplements may be hardly digestible, reduce peristalsis, by causing the stomach and intestine to swell, and over-fatigue or damage the liver and kidneys that cannot fully remove excess proteins.

The international application WO2004/014153 and the European patent application EP-A-1604677 disclose examples of known, dietary supplements.

SUMMARY OF THE INVENTION

The present invention has the object of obviating the drawbacks of classical weight loss low calorie diets by providing a dietary supplement that can avoid prior art drawbacks and allow natural weight loss.

A further object is to provide a dietary supplement that has a high protein contents while being easily digestible and assimilable by the body.

Yet another object is to provide a dietary supplement that increases metabolism and supports proper operation of the intestine and peristalsis.

Yet another object is to conceive a dietary supplement that prevents swelling of the stomach and intestine, and avoids the disorders and cosmetic problems associated thereto.

Another important object is to provide a dietary supplement that has depurative health-promotion properties.

Finally, the invention has the object of providing a dietary supplement that is palatable, unalterable when cooked and that can be introduced in daily meals in the preparation of soups, fresh pasta, bread, pizza, seasonings and snacks.

These objects are fulfilled by a dietary protein-based supplement described herein.

Thanks to the provision of the plant-based protein activator, the high protein content of the Integrator can be assimilated without causing damage to the body.

The protein activator of the invention comprises a first group of plant extracts with proteolytic activity, obtained from the fruit or stalk of plants selected from the group comprising papaya, pineapple, sundew.

Thanks to the proteolytic activity of this first group of extracts, the proteins in the mixture will be easily digested.

The protein activator of the invention comprises a second group of plant extracts with an emollient and peristaltic activity, a third group of plant extracts with a carminative activity and a fourth group of plant extracts with a depurative and liver and kidney protective activity.

Thanks to these plant extracts and their activities, optimal body operation will be maintained and no damage will be caused to the stomach, intestine, liver or kidneys.

According to one aspect, use of a dietary supplement for the preparation of dietary foods is provided, said dietary supplement comprising a base mixture of ingredients with at least one plant or animal protein and a plant-based protein activator consisting of:

proteolytic extracts obtained from the sap or the fruit or stalk of a first group of plants selected from the group consisting of papaya, pineapple, sundew;

emollient and peristaltic extracts obtained from the leaves, bark, roots or rhizomes of a second group of plants selected from the group consisting of senna, mallow, cascara, frangula, rhubarb, curly dock, aloe;

carminative extracts obtained from the leaves, fruits, roots and rhizomes of a third group of plants selected from the group consisting of star anise, green anise, fennel, ginger, mint, turmeric;

depurative and liver and kidney protective extracts obtained from the leaves, fruits, roots and rhizomes of a fourth group of plants selected from the group consisting of artichoke, dandelion, boldo, radish, burdock, milk thistle;

wherein:

a weight content of each proteolytic extract of said first group of plants is from 0.4% to 2.8%, based on the total weight of the supplement;

a weight content of each emollient and peristaltic extract of said second group of plants is from 0.05% to 1.4%, based on a total weight of the supplement;

a weight content of each carminative extract of said third group of plants is from 0.2% to 1.4%, based on the total weight of the supplement;

a weight content of each depurative and liver and kidney protective extract of said fourth group of plants is from 0.1% to 0.6%, based on the total weight of the supplement.

According to another aspect, dietary foods comprising a dietary supplement are provided comprising a base mixture of ingredients with at least one plant or animal protein and a plant-based protein activator consisting of:

proteolytic extracts obtained from the sap or the fruit or stalk of a first group of plants selected from the group consisting of papaya, pineapple, sundew;

emollient and peristaltic extracts obtained from the leaves, bark, roots or rhizomes of a second group of plants selected from the group consisting of senna, mallow, cascara, frangula, rhubarb, curly dock, aloe;

carminative extracts obtained from the leaves, fruits, roots and rhizomes of a third group of plants selected from the group consisting of star anise, green anise, fennel, ginger, mint, turmeric;

depurative and liver and kidney protective extracts obtained from the leaves, fruits, roots and rhizomes of a fourth group of plants selected from the group consisting of artichoke, dandelion, boldo, radish, burdock, milk thistle;

wherein:

a weight content of each proteolytic extract of said first group of plants is from 0.4% to 2.8%, based on the total weight of the supplement;

a weight content of each emollient and peristaltic extract of said second group of plants is from 0.05% to 1.4%, based on a total weight of the supplement;

a weight content of each carminative extract of said third group of plants is from 0.2% to 1.4%, based on the total weight of the supplement;

a weight content of each depurative and liver and kidney protective extract of said fourth group of plants is from 0.1% to 0.6%, based on the total weight of the supplement.

DETAILED DESCRIPTION OF PREFERRED EMBODIMENTS

The dietary protein supplement of the invention essentially comprises a base mixture of ingredients with at least one plant or animal protein and a plant-based protein activator.

The base mixture may include one or more plant or animal proteins selected from the group of proteins from soybean, peas, eggs, milk, as well as simple and complex glucides, lipids, fibers, minerals.

The supplement is introduced in a diet plan known as "tisanoreica®" which largely uses products and extracts obtained by decotion, and will be referred to hereafter as "tisanoreica® supplement".

According to the invention, the plant-based protein activator or tisanoreica® activator may comprise a first group of plant extracts with proteolytic activity, obtained from plants selected from the group comprising papaya (*Carica Papaia* L.), pineapple (*Ananas Comosus* L.Merr.), sundew (*Drosera rotundifolia* L.).

Particularly, the papaya fruit, and namely its sap, contains a mixture of proteolytic enzymes, such as papain and chymopapain, which specifically hydrolyzes polypeptides containing basal amino acids, leucine and glycine. The fruit and stem of the pineapple contain a mixture of proteolytic enzymes, known as "bromelain" which has anti-inflammatory, cicatrizing and fibrinolytic properties, in addition to the ability to hydrolyze proteins to oligopeptides and amino acids. A mixture of proteolytic enzymes may be also obtained from the whole plant of sun dew.

The optimal weight content of each plant extract from papaya, pineapple or sundew is from 0.4% to 2.8% and preferably about 0.9%, based on the total weight of the supplement. The weight content of each plant extract from papaya, pineapple or sundew is from 0.8% to 4% and preferably about 1.3%, based on the total weight of the proteins of the base mixture.

The plant-based protein activator or tisanoreica® activator of to invention may comprise a second group of plant extracts with peristaltic activity, obtained from plants selected from the group comprising senna (*Cassia Fistula* L.), mallow (*Malva* L.), cascara (*Rhamnus purshiana*), frangula (*Rhamnus frangula*), rhubarb (*Rheum officinale* L.), curly dock (*Rumex crispus*), aloe (*Aloe vera harborescens*).

Particularly, the leaves of senna contain anthraquinone derivatives (sennosides A and B) which cause contraction of smooth muscles, and a consequent increase of peristaltic activity. Mallow leaves contain mucilages, anthocyanins, caffeic acid and chlorogenic acid which have emollient and sedative properties.

Other plants with emollient activity, such as licorice (*Glycyrrhiza glabra*), elm (*Ulma rubra*), marshmallow (*Altea officinalis*) calendula (*Calendula officinalis*) and chamomile (*Matricaria camomilla*) may be used in combination with or instead of mallow.

It was experimentally found that an optimal weight content of each plant extract of the second group with peristaltic and emollient activity is from 0.05% to 1.4% and preferably from 0.1 to 0.45%, based on the total weight of the supplement. Such weight content is from 0.10% to 1.95% and preferably from 0.15% to 0.65% based on the total weight of the proteins of the mixture. Due to the property of increasing water in the intestine, the weight content of senna has to be particularly small, i.e. of the order of 0.1% based on the total weight of the supplement or 0.13% based on the total weight of the proteins.

The plant-based protein activator or tisanoreica® activator of the invention may further comprise a third group of plant extracts with carminative activity, obtained from plants selected from the group comprising star anise (*Illicium verum*), green anise (*Pimpinella anisum*), fennel (*Foeniculum vulgare* Mill.), ginger (*Zingiber officinalis*), mint (*Menta X piperita*), turmeric (*curcuma longa* L.).

It was experimentally found that the weight content of each plant extract of said third group with carminative activity is from 0.2% to 1.4% and preferably about 0.5% when based on the total weight of the supplement, and from 0.3% to 2%, preferably about 0.6%, when based on the total weight of proteins.

Finally, the plant-based dietary protein supplement and tisanoreica® activator of the invention may comprise a fourth group of plant extracts with depurative and liver and kidney protective activity, which can promote secretion and synthesis of bile (choleretic plants and cholagogues) selected from the group comprising artichoke (*Cynara scolimus*), dandelion (*Taraxacum officinale*), boldo (*Peumus boldus* Mol.), radish (*Raphanus sativus*), burdock (*Arctium lappa* L.), milk thistle (*Silybum marianum*), turmeric (*Curcuma longa* L.).

The weight content for the plant extracts of this group with depurative and liver and kidney protective activity is from 0.1% to 0.6% and preferably about 0.25% when based on the total weight of the supplement, and from 0.15% to 2%, preferably about 0.30%, when based on the total weight of proteins.

The plant extracts of the plant-based activator or tisanoreica® activator of the invention may be prepared in the form of dried, micronized or freeze-dried powder, or in a wet state and in the form of infusions, herb teas, suspensions in non-polar solvents such as resins and oils.

The base mixture may include one or more plant or animal proteins selected from the group of proteins from soybean, peas, eggs, milk, as well as other ingredients selected from the group comprising simple and complex glucides, lipids, fibers, minerals.

The example below will allow those of ordinary skill in the art to implement the invention in every aspect.

EXAMPLE

A dietary supplement was prepared in accordance with the following table, which lists the components of the base mixture and the protein activator, as well as their respective weight contents based on the total weight and, for the activator, based on the total weight of the proteins.

| COMPONENT | weight %/total | weight %/proteins |
|---|---|---|
| BASE MIXTURE | | |
| Proteins | 71.0 | |
| Simple glucides | 11.4 | |
| Complex glucides | 2.2 | |
| Fibers | 6.4 | |
| Lipids | 1.2 | |
| Minerals | 1.2 | |
| PROTEIN ACTIVATOR | | |
| Papaya | 0.90 | 1.26 |
| Pineapple | 0.90 | 1.26 |
| Mallow | 0.40 | 0.56 |
| Senna | 0.09 | 0.12 |
| Star Anise | 0.45 | 0.63 |
| Fennel | 0.45 | 0.63 |
| Artichoke | 0.18 | 0.25 |
| Dandelion | 0.18 | 0.25 |

The dietary supplement of the invention is susceptible of a many changes and variants within the inventive principle disclosed in the annexed claims. All the details thereof may be replaced by other technically equivalent parts, and the materials may vary depending on different needs, without departure from the scope of the invention.

What is claimed is:

1. A method of promoting weight loss, wherein said method comprises administering to a subject in need thereof an effective amount of a dietary supplement comprising a base mixture of ingredients with at least one plant or animal protein and a plant-based protein activator consisting of:
   proteolytic extracts obtained from the sap or the fruit or stalk of a first group of plants selected from the group consisting of papaya, pineapple and sundew;
   emollient and peristaltic extracts obtained from the leaves, bark, roots or rhizomes of a second group of plants selected from the group consisting of senna, mallow, cascara, frangula, rhubarb, curly dock and aloe;
   carminative extracts obtained from the leaves, fruits, roots and rhizomes of a third group of plants selected from the group consisting of star anise, green anise, fennel, ginger, mint and turmeric;
   depurative and liver and kidney protective extracts obtained from the leaves, fruits, roots and rhizomes of a fourth group of plants selected from the group consisting of artichoke, dandelion, boldo, radish, burdock and milk thistle;
   wherein:
   a weight content of each proteolytic extract of said first group of plants is from 0.4% to 2.8%, based on the total weight of the supplement;
   a weight content of each emollient and peristaltic extract of said second group of plants is from 0.05% to 1.4%, based on a total weight of the supplement;
   a weight content of each carminative extract of said third group of plants is from 0.2% to 1.4%, based on the total weight of the supplement;
   a weight content of each depurative and liver and kidney protective extract of said fourth group of plants is from 0.1% to 0.6%, based on the total weight of the supplement.

2. The method as claimed in claim 1, wherein the weight content of each proteolytic extract of said first group of plants is from 0.4% to 4%, based on the total weight of the proteins of the mixture.

3. The method as claimed in claim 2, wherein the weight content of each proteolytic extract of said first group of plants is about 1.3%, based on the total weight of the proteins of the mixture.

4. The method as claimed in claim 1, wherein the weight content of each emollient and peristaltic extract of said second group of plants is from 0.10% to 1.95%, based on the total weight of the proteins of the mixture.

5. The method as claimed in claim 4, wherein the weight content of each emollient and peristaltic extract of said second group of plants is from 0.15% to 0.65%, based on the total weight of the proteins of the mixture.

6. The method as claimed in claim 1, wherein the weight content of each carminative extract of said third group of plants is from 0.3% to 2%, based on the total weight of the proteins of the mixture.

7. The method as claimed in claim 6, wherein the weight content of each carminative extract of said third group of plants is about 0.6%, based on the total weight of the proteins of the mixture.

8. The method as claimed in claim 1, wherein the weight content of each depurative and liver and kidney protective extract of said fourth group of plants is from 0.15% to 2%, based on the total weight of the proteins of the mixture.

9. The method as claimed in claim 8, wherein the weight content of each depurative and liver and kidney protective extract of said fourth group of plants is about 0.30%, based on the total weight of the proteins of the mixture.

10. The method as claimed in claim 1, wherein the weight content of each proteolytic extract of said first group of plants is 0.9% based on the total weight of the supplement.

11. The method as claimed in claim 1, wherein the weight content of each emollient and peristaltic extract of said second group of plants is from 0.1% to 0.45%, based on the total weight of the supplement.

12. The method as claimed in claim 1, wherein the weight content of each carminative extract of said third group of plants is 0.5% based on the total weight of the supplement.

13. The method as claimed in claim 1, wherein the weight content of each depurative and liver and kidney protective extract of said fourth group of plants is 0.25% based on the total weight of the supplement.

14. The method as claimed in claim 1, wherein the extracts of said activator are prepared in a form of dried, micronized or freeze-dried powder, or in a wet state and in the form of infusions, herb teas, suspensions in non-polar solvents, resins and oils.

15. The method as claimed in claim 1, wherein said at least one plant or animal protein of said base mixture is selected from the group consisting of proteins from soybean, peas, eggs and milk.

16. The method as claimed in claim 1, wherein said base mixture of ingredients comprises additives selected from the group consisting of polydextrose, chlorogenic acid, maltodextrins, silicon dioxide, thickeners, anticaking agents, stabilizers, sweeteners, acidity regulators, phenylalanine and natural flavors for allowing it to be used in the preparation of easily digestible high-protein dietary food.

17. The method as claimed in claim 1, wherein the proteolytic extracts contain a mixture of proteolytic enzymes, including papain and chymopapain, which specifically hydrolyzes polypeptides containing basal amino acids, leucine and glycine and/or a mixture of proteolytic enzymes, including bromelain which has anti-inflammatory, cicatrizing and fibrinolytic properties, in addition to the ability to hydrolyze proteins to oligopeptides and amino acids.

18. The method as claimed in claim 1, wherein the emollient and peristaltic extracts contain anthraquinone derivatives, including sennosides A and B, which cause contraction of smooth muscles, and a consequent increase of peristaltic activity, and/or mucilages, anthocyanins, caffeic acid and chlorogenic acid which have emollient and sedative properties.

19. The method according to claim 1 for introduction in daily meals.

* * * * *